(12) United States Patent
Hosoi et al.

(10) Patent No.: US 6,923,541 B2
(45) Date of Patent: Aug. 2, 2005

(54) OPTOMETRIC APPARATUS

(75) Inventors: Yoshinobu Hosoi, Gamagori (JP); Akihiro Hayashi, Toyokawa (JP)

(73) Assignee: NIDEK Co., Ltd., Gamagori (JP)

( * ) Notice: Subject to any disclaimer, the term of this patent is extended or adjusted under 35 U.S.C. 154(b) by 79 days.

(21) Appl. No.: 10/280,020

(22) Filed: Oct. 25, 2002

(65) Prior Publication Data

US 2003/0081175 A1 May 1, 2003

(30) Foreign Application Priority Data

Oct. 31, 2001 (JP) ........................................ 2001-335869
Oct. 31, 2001 (JP) ........................................ 2001-335870

(51) Int. Cl.[7] ............................................... A61B 3/02
(52) U.S. Cl. ................................................. 351/235
(58) Field of Search ................................. 351/200, 205, 351/216, 217, 222, 227, 229, 233, 234, 235

(56) References Cited

U.S. PATENT DOCUMENTS

| 4,798,457 A | 1/1989 | Morohashi et al. |
| 5,648,833 A | 7/1997 | Doms et al. |
| 5,812,241 A | 9/1998 | Doms et al. |

FOREIGN PATENT DOCUMENTS

| FR | 2 478 459 | * | 9/1981 |
| JP | A 9-149886 | | 6/1997 |
| JP | A 11-267100 | | 10/1999 |

\* cited by examiner

*Primary Examiner*—Brian L. Casler
*Assistant Examiner*—John R. Sanders
(74) *Attorney, Agent, or Firm*—Oliff & Berridge, PLC (57) ABSTRACT

An optometric apparatus for a subjective examination of a visual function of an examinee's eye includes a pair of right-and-left lens chamber units, each having test windows; and rotary disks disposed in each unit, each disk holding therein optical elements, one of the optical elements in each disk being placed between the test windows; and the optical elements include optical elements of 29 mm to 39 mm in effective diameter.

13 Claims, 10 Drawing Sheets

|       | 1 | 2                      | 3      | 4     | 5                        | 6     |
|-------|---|------------------------|--------|-------|--------------------------|-------|
| H-SPH | 0 | -9.00                  | -18.00 | BL    | +18.00                   | +9.00 |
| M-SPH | 0 | -1.50                  | -3.00  | -4.50 | +3.00                    | +1.50 |
| L-SPH | 0 | -0.25                  | -0.50  | -0.75 | +0.50                    | +0.25 |
| AUX 1 | 0 | 6Δ for R<br>10Δ for L  | PH     | MR    | Red for R<br>Green for L | Pola  |
| H-CYL | 0 | -1.50                  | -3.00  | -4.50 | -6.00                    | -7.50 |
| L-CYL | 0 | -0.25                  | -0.50  | -0.75 | -1.00                    | -1.25 |
| AUX 2 | 0 | RP                     | S+10   | S-10  | ±0.25AXC                 | PD    |

FIG. 8

|       | 1 | 2     | 3      | 4      | 5                       | 6     |
|-------|---|-------|--------|--------|-------------------------|-------|
| H-SPH | 0 | -9.00 | -18.00 | BL     | +18.00                  | +9.00 |
| M-SPH | 0 | -1.50 | -3.00  | -4.50  | +3.00                   | +1.50 |
| L-SPH | 0 | -0.25 | -0.50  | -0.75  | +0.50                   | +0.25 |
| AUX   | 0 | PD    | PH     | ±0.5XC | Red for R<br>Green for L | Pola  |
| H-CYL | 0 | -1.50 | -3.00  | -4.50  | -6.00                   | -7.50 |
| L-CYL | 0 | -0.25 | -0.50  | -0.75  | -1.00                   | -1.25 |

FIG. 9A

|       | 1 | 2     | 3      | 4     | 5      | 6     |
|-------|---|-------|--------|-------|--------|-------|
| H-SPH | 0 | -9.00 | -18.00 | BL    | +18.00 | +9.00 |
| M-SPH | 0 | -1.50 | -3.00  | -4.50 | +3.00  | +1.50 |
| L-SPH | 0 | -0.25 | -0.50  | +0.75 | +0.50  | +0.25 |

FIG. 9B

|       | 1 | 2     | 3      | 4     | 5      | 6     |
|-------|---|-------|--------|-------|--------|-------|
| H-SPH | 0 | -9.00 | -18.00 | BL    | +18.00 | +9.00 |
| M-SPH | 0 | -1.50 | -3.00  | -4.50 | +3.00  | +1.50 |
| L-SPH | 0 | -0.25 | -0.50  | -0.75 | -1.00  | +0.25 |

FIG. 9C

|       | 1 | 2     | 3      | 4     | 5      | 6     |
|-------|---|-------|--------|-------|--------|-------|
| H-SPH | 0 | -9.00 | -18.00 | BL    | +18.00 | +9.00 |
| M-SPH | 0 | -1.50 | -3.00  | -4.50 | +3.00  | +1.50 |
| L-SPH | 0 | -0.25 | -0.50  | -0.75 | -1.00  | -1.25 |

FIG. 9D

|       | 1 | 2     | 3      | 4     | 5      | 6     |
|-------|---|-------|--------|-------|--------|-------|
| H-SPH | 0 | -9.00 | -18.00 | BL    | +18.00 | +9.00 |
| M-SPH | 0 | -1.50 | -3.00  | -4.50 | +3.00  | +1.50 |
| L-SPH | 0 | -0.25 | +1.00  | +0.75 | +0.50  | +0.25 |

FIG. 9E

|       | 1 | 2     | 3      | 4     | 5      | 6     |
|-------|---|-------|--------|-------|--------|-------|
| H-SPH | 0 | -9.00 | -18.00 | BL    | +18.00 | +9.00 |
| M-SPH | 0 | -1.50 | -3.00  | -4.50 | +3.00  | +1.50 |
| L-SPH | 0 | +1.25 | +1.00  | +0.75 | +0.50  | +0.25 |

FIG. 9F

|       | 1 | 2     | 3      | 4     | 5      | 6     |
|-------|---|-------|--------|-------|--------|-------|
| H-SPH | 0 | -9.00 | -18.00 | BL    | +18.00 | +9.00 |
| M-SPH | 0 | -1.50 | -3.00  | +4.50 | +3.00  | +1.50 |
| L-SPH | 0 | -0.25 | -0.50  | +0.75 | +0.50  | +0.25 |

FIG. 9G

|       | 1 | 2     | 3      | 4     | 5      | 6     |
|-------|---|-------|--------|-------|--------|-------|
| H-SPH | 0 | -9.00 | -18.00 | BL    | +18.00 | +9.00 |
| M-SPH | 0 | -1.50 | -3.00  | +4.50 | +3.00  | +1.50 |
| L-SPH | 0 | -0.25 | +1.00  | +0.75 | +0.50  | +0.25 |

FIG. 10

| | 1 | 2 | 3 | 4 | 5 | 6 | 7 | 8 | 9 | 10 | 11 | 12 |
|---|---|---|---|---|---|---|---|---|---|---|---|---|
| H-SPH | 0 | -3.00 | -6.00 | -9.00 | -12.00 | -15.00 | -18.00 | +15.00 | +12.00 | +9.00 | +6.00 | +3.00 |
| M-SPH | 0 | -0.25 | -0.50 | -0.75 | -1.00 | +1.75 | +1.50 | +1.25 | +1.00 | +0.75 | +0.50 | +0.25 |
| H-CYL | 0 | -1.50 | -3.00 | -4.50 | -6.00 | -7.50 | | | | | | |
| L-CYL | 0 | -0.25 | -0.50 | -0.75 | -1.00 | -1.25 | | | | | | |
| AUX 1 | 0 | 0.12 | P135 | P45 | P+0.12 | P+0.12 | MR | R/G | 6/10Δ | ±0.5XC | PH | BL |
| AUX 2 | 0 | RP | ±0.25XC | ±0.5XC | ±0.25AXC | -10 | +10 | PD | | | | |

US 6,923,541 B2

OPTOMETRIC APPARATUS

BACKGROUND OF THE INVENTION

1. Field of the Invention

The present invention relates to an optometric apparatus for a subjective examination of a visual function of an examinee's eye.

2. Description of Related Art

There is an optometric apparatus provided with a pair of right-and-left lens chamber units in each of which rotary disks are disposed, each disk mounting therein various types of optical elements (a spherical lens, a cylindrical lens, and an auxiliary lens such as a prism and a filter).

Each optical element provided in the conventional optometric apparatus of the above type is 20 mm in diameter (19 mm in effective diameter). However, when an examinee views an examination optotype through the optical element of such size, accommodation by a peeping effect (so-called mechanical myopia) may intervene, which causes an inaccurate examination result. After the examination using the above optometric apparatus, therefore, a trial frame examination using a trial lens of a relatively larger size is generally conducted. As a result, it would take much time to get through the examination.

Figure 10:
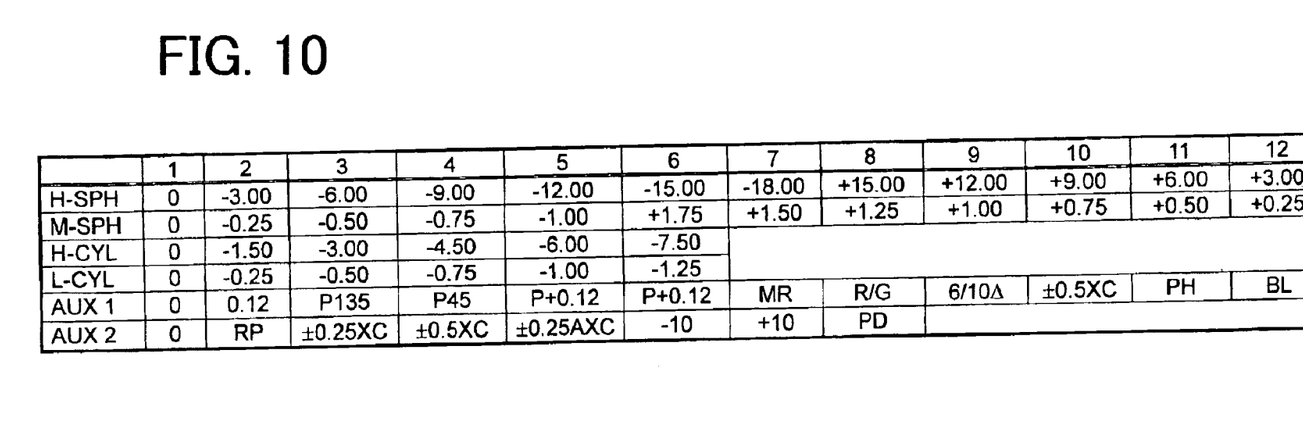
FIG. 10 is a table showing arrangements of optical elements in the disk arrangement in a conventional optometric apparatus.

The arrangement of the optical elements in each disk is, for example, as shown in FIG. 10. The structure in FIG. 10 includes two disks for the spherical lenses, two disks for the cylindrical lenses, and two disks for the auxiliary lenses. For instance, with regard to the spherical lens disks, two lenses one each of which is selected from eleven spherical lenses arranged in each disk can produce powers (diopters) of −19.00D to +16.75D in increments of 0.25D. A shielding plate (BL) to be used in an examination for one eye is arranged in the auxiliary lens disk which is the fifth disk far from the examinee's eye. However, this arrangement of the shielding plate would allow disturbance light to enter the inside of the lens chamber unit through a test window disposed on the examinee's eye side. Accordingly, movements of the optical elements (disks) disposed on the near side of the shielding plate to the examinee's eye and a superfluous internal structure could be seen by the examinee. Thus, the examinee might feel so uncomfortable as to have trouble in concentrating on the examination.

SUMMARY OF THE INVENTION

The present invention has been made in view of the above circumstances and has an object to overcome the above problems and to provide an optometric apparatus which enables execution of an accurate examination.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an optometric apparatus for a subjective examination of a visual function of an examinee's eye, including: a pair of right-and-left lens chamber units, each having test windows; and rotary disks disposed in each unit, each disk holding therein optical elements, one of the optical elements in each disk being placed between the test windows; wherein the optical elements include optical elements of 29 mm to 39 mm in effective diameter.

According to another aspect of the present invention, there is provided an optometric apparatus for a subjective examination of a visual function of an examinee's eye, including: a pair of right-and-left lens chamber units, each having test windows; rotary disks disposed in each unit, each disk holding therein optical elements, one of the optical elements in each disk being placed between the test windows; and a shielding plate arranged as the optical element in the disk disposed in the closest position to the examinee's eye.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
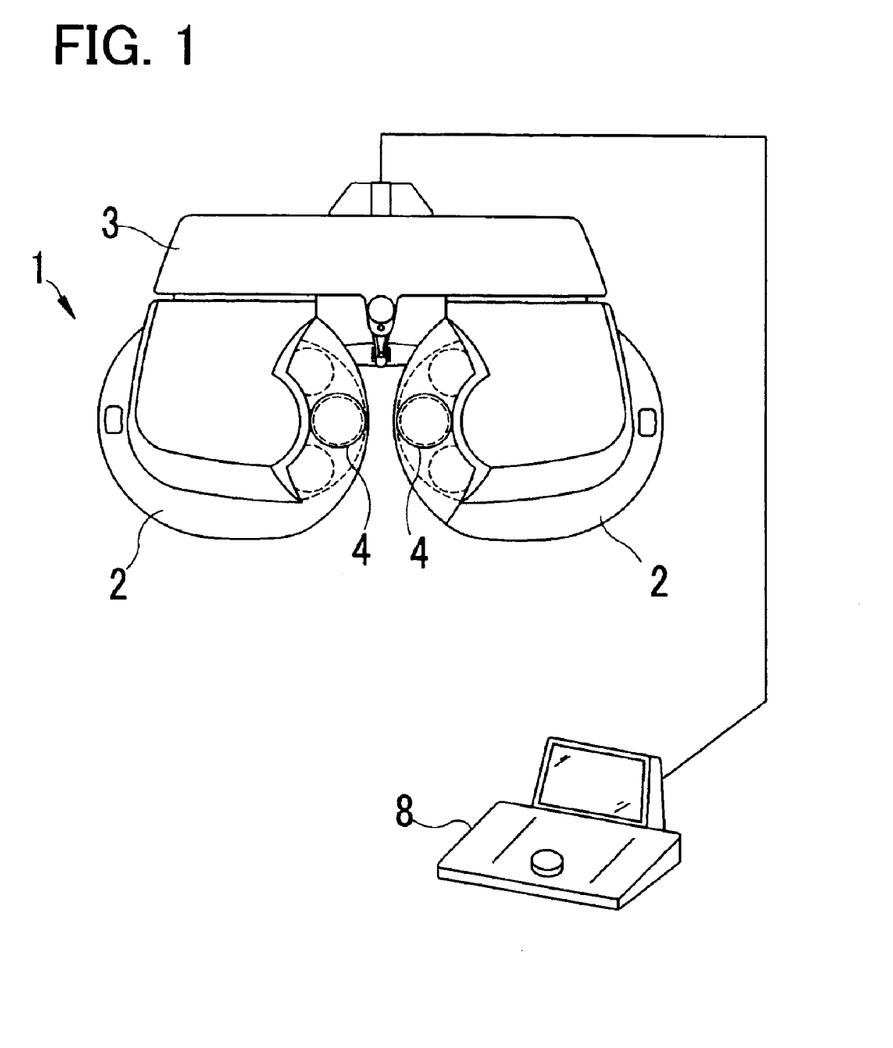
FIG. 1 is a front view of an outer appearance of an optometric apparatus in an embodiment according to the present invention, seen from an examiner's side.

A detailed description of a preferred embodiment of an optometric apparatus embodying the present invention will now be given referring to the accompanying drawings. FIG. 1 is a front view of an outer appearance of a subjective optometric apparatus in the present embodiment, seen from an examiner's side.

Numeral 1 is a main unit of the optometric apparatus, which includes a pair of symmetrical right-and-left lens chamber units 2, a moving unit 3 which supports the pair of units 2 and has a function of adjusting a distance between the units 2 and another function of converging the units 2, and a test window 4 provided in each lens chamber unit 2. Numeral 8 is a controller for operating the main unit 1.

Figure 2:
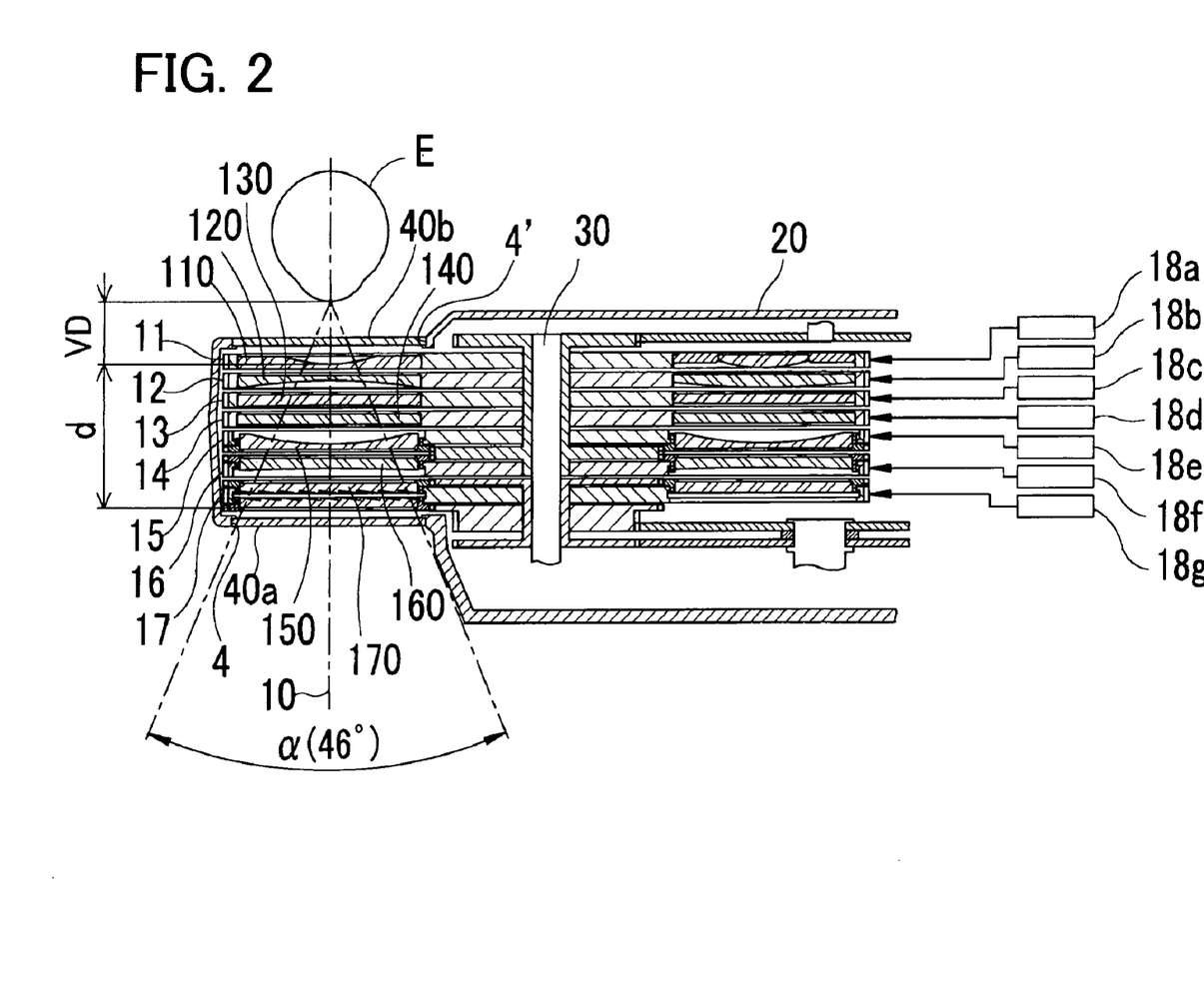
FIG. 2 is a partial section view of a lens chamber unit for a left eye examination, seen from above, showing a disk arrangement.

FIG. 2 is a partial section view of the lens chamber unit 2 to be used for a left eye examination, seen from above, showing a disk arrangement. Numeral 10 is an optical axis for examination. Alphabet E denotes an examinee's eye. In a case 20 of the lens chamber unit 2, there are disposed seven disks 11 to 17 which are rotatable about a shaft 30. Each disk is provided with circumferentially arranged holes and a plurality of optical elements held in respective holes. Those disks are disposed in the following order from a closer position to the examinee's eye E; a high-power spherical lens disk 11, a moderate-power spherical lens disk 12, a low-power spherical lens disk 13, a first auxiliary lens disk 14, a high-power cylindrical lens disk 15, a low-power cylindrical lens disk 16, a second auxiliary lend disk 17. Each disk is formed with a gear in the periphery. Each gear is operated by a corresponding motor 18a, 18b, 18c, 18d, 18e, 18f, or 18g to switch an optical element to be brought in alignment with the optical axis 10. In FIG. 2, numeral 40a is a protective glass fit in the test window 4 for the examiner's eye, and numeral 40b is a protective glass fit in a test window 4' for the examinee's eye E.

Figure 6:
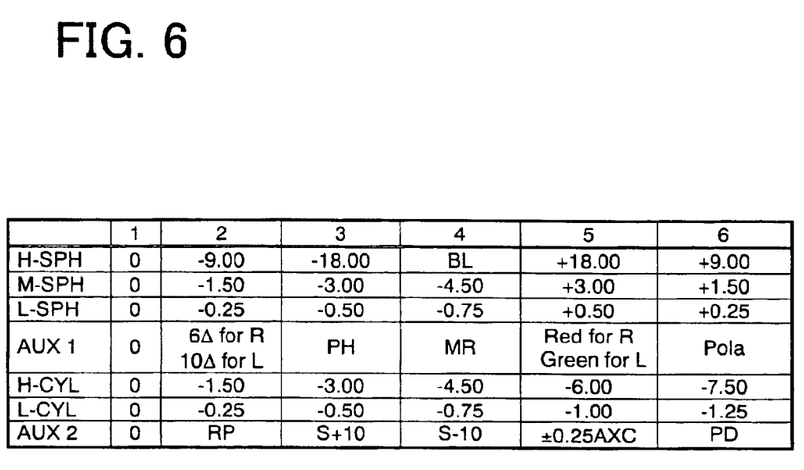
FIG. 6 is a table showing arrangements of optical elements in the disk arrangement in FIG. 2.

The disks 11 to 17 each have five to eight holes for holding optical elements individually. In the present embodiment, each disk has six holes. The arrangements of the optical elements in this case are shown in FIG. 6. Each disk has a single plain opening (including the case of a lens of 0D). The disks 11, 12, and 13 hold spherical lenses respectively. The disk 11 is to hold high-power spherical lenses (H-SPH) 110 including spherical lenses of −9D (hereafter, "D" means diopter), −18D, +9D, +18D and a shielding plate (BL), which are arranged in five holes other than the opening. The disk 12 is to hold moderate-power spherical lenses (M-SPH) 120 including spherical lenses of −1.5D, −3D, −4.5D, +3D, +1.5D, which are arranged in five holes other than the opening. The disk 13 is to hold low-power spherical lenses (L-SPH) 130 including −0.25D, −0.5D, −0.75D, +0.5D, +0.25D, which are arranged in five holes other than the opening.

The disk 14 is to hold a first group of auxiliary lenses (AUX1) 140 including a dispersion prism (10Δbase in for a left eye and 6Δbase up for a right eye), a pinhole (PH), a Maddox lens (MR), a green filter (a red filter for a right eye), and a polarizing plate (Pola), which are arranged in five holes other than the opening. These first group auxiliary lenses 140 are configured not to rotate about the optical axis 10.

The disk 15 is to bold high-power cylindrical lenses H-CYL) 150 including cylindrical lenses of −7.50D to −1.50D in increments of 1.5D, which are arranged in five holes other than the opening. The disk 16 is to hold lower-power cylindrical lenses (L-CYL) 160 including cylindrical lenses of −1.25D to −0.25D in increments of 0.25D, which are arranged in five holes other than the opening. The cylindrical lenses 150 and 160 are rotatably arranged respectively about the optical axis 10.

The disk 17 is to hold a second group of auxiliary lenses (AUX2) 170 including a rotary prism (RP), a spherical lens of +10D, a spherical lens of −10D, an auto-cross-cylinder lens (AXC) of ±0.25D, and a plain lens (PD) attached with a mark for adjustment of a distance between eyes (i.e., an interpupillary distance), which are arranged in five holes other than the opening. Of these auxiliary lenses 170, the rotary prism and the auto-cross-cylinder lens are rotatably arranged about the optical axis 10.

Figure 3:
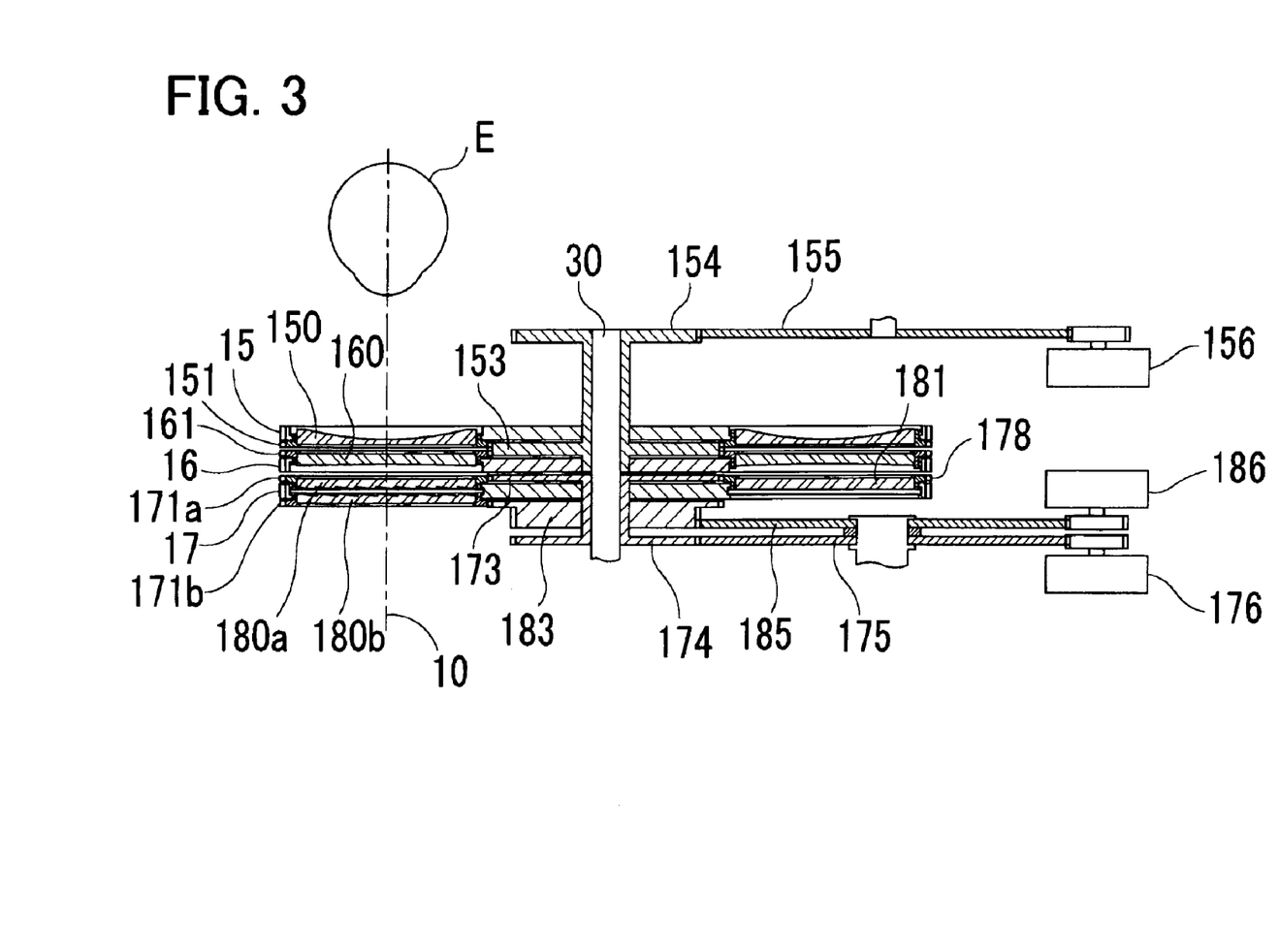
FIG. 3 is an explanatory view showing a rotary mechanism of optical elements.

FIG. 3 is an explanatory view to explain a rotary mechanism of the optical elements provided in the disks 15, 16, and 17. The cylindrical lenses 150 held in the holes of the disk 15 are attached thereto by a holder 151 having a gear so that the lenses 150 are rotatable about the optical axis 10. The cylindrical lenses 160 held in the holes of the disk 16 are attached thereto by a holder 161 having a gear so that the lenses 160 are rotatable about the optical axis 10. The gears of the holders 151 and 161 are individually engaged with a sun gear 153 rotatable about a shaft 30. The rotation of a motor 156 is thus transmitted to the cylindrical lenses 150 and 160 at the same time through a gear 154 joined to the sun gear 153 and an intermediate gear 155.

Of the auxiliary lenses 170 held in the disk 17, two rotary prisms 180a and 180b and the auto-cross-cylinder lens 181 are rotatably provided about the optical axis 10. The rotary prism 180a arranged closer to the examinee's eye is rotatably attached by a holder 171a having a gear and the other rotary prism 180b is rotatably attached by a holder 171b having a gear. The auto-cross-cylinder lens 181 is rotatably attached by a holder 178 having a gear. The gears of the holders 171a and 178 are engaged with a sun gear 173 rotatable about the shaft 30. The rotation of a motor 176 is thus transmitted to the holders 171a and 178 through a gear 174 joined to the sun gear 173 and an intermediate gear 175. The gear of the holder 171b is engaged with another sun gear 183, not the sun gear 173. A gear integrally formed in the sun gear 183 is connected to a motor 186 through an intermediate gear 185. The rotation of the motor 186 is thus transmitted to the holder 171b.

Each optical element held in the disks 11 to 17 is of a large diameter which is basically 30 mm to 40 mm (29 mm to 39 mm in effective diameter). Preferably, the lens diameter is 36 mm or more (35 mm or more in effective diameter) to be used in a general examination using a trial frame. In the present embodiment, lenses of 35 mm in effective diameter are used. The examinee is requested to observe an examination optotype presented in alignment with the optical axis 10 through the optical elements of large diameter.

By use of such lenses of large diameter, the angle α of a visual field of the examinee's eye E can be widened as compared with a conventional lens of 19 mm in effective diameter. During an eye examination (optometry), a distance VD between a corneal apex of the examinee's eye E and the spherical lens 110 held in the disk 11 disposed in the closest position to the examinee's eye E is adjusted to a predetermined distance (mostly 12 mm in Japan). The visual angle α of the examinee's eye E is determined based on the effective diameter of the auxiliary lens 170 in the disk 17 disposed in the farthest position from the examinee's eye E and a lens distance d from the spherical lens 110 to the auxiliary lens 170. The effective diameter and the lens distance are set so that the visual angle α is 40° or more, preferably, 45° or more. Assuming that the effective diameter of the optical element is 35 mm and the lens distance d is 28 mm, the visual angle α of 46° can be ensured. The lens diameter of the protective glass 40a provided in the test window 4 is set larger than that of the optical elements to ensure the above visual angle α.

As the diameter of a lens or prism having refractive power increases, however, the thickness of the lens or prism increases. The increase in thickness of the optical element results in a long lens distance d, which counts against widening the visual angle α. To suppress the increase in thickness of the optical element, the following structure is adopted.

Figure 4A:
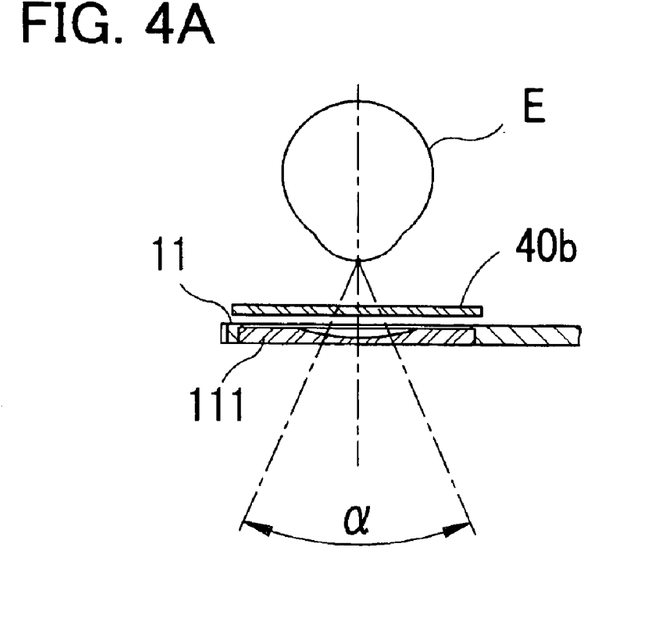
FIGS. 4A and 4B are explanatory views showing structures to reduce each thickness of a minus-power spherical lens and a plus-power spherical lens.

FIG. 4A shows a spherical lens 111 of a minus power, held in the disk 11. With regard to the minus power spherical lens, the increase in lens diameter causes the increase in thickness of a peripheral part of the lens. To prevent such a disadvantage, the minus power spherical lens 111 in the present embodiment is designed so that an optical region having a refractive power is provided for at least a range of the visual angle α while the peripheral part is cut in a flat form or chamfered largely so that the thickness is 3 mm or less. In the present embodiment, the thickness is set to 2.5 mm. To suppress each thickness of the minus power cylindrical lenses 150 and 160, similarly, the same configuration as above may be applied to those lenses.

Figure 4B:
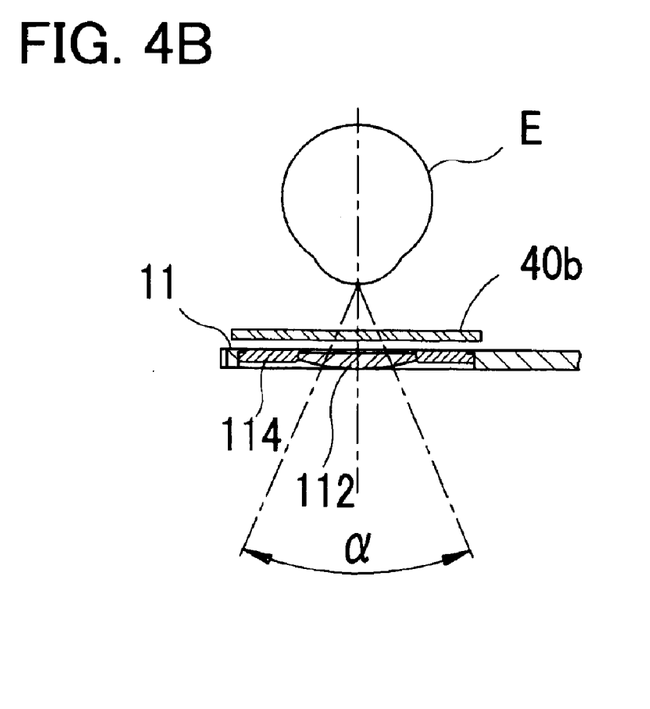

FIG. 4B Shows a spherical lens 112 of a plus power, held in the disk 11. A plus power spherical lens generally has a center part thicker than a peripheral part. If the thickness of the center part of the high plus power spherical lens is suppressed, a necessary effective diameter could not be ensured (including the case where the thickness of the peripheral part becomes too thin) and consequently this lens could not be held directly by the hole of the disk 11. As a measure to this, the plus power spherical lens 112 in the present embodiment is designed to have a lens diameter to retain an optical region having a refractive power within the range of at least the visual angle α and a holder 114 made of a transparent material is used to cover the shortage in diameter of the lens 112 with respect to the hole diameter of the disk 11 so that the lens 112 is held by the disk 11 through the holder 114. It is to be noted that the holder 114 and the lens 112 may be formed integrally. Alternatively, the holder 114 and the disk 11 may be made integrally of a transparent material. As with the minus power spherical lens, the plus power spherical lens is also designed to have the thickness of 3 mm or less, preferably, 2.5 mm or less. The minus power spherical lens may also be configured using the transparent holder 114.

An optical element which has the largest thickness due to an increase in lens diameter is a prism to be used in a heterophoria test. When a general prism having a triangular section is used, the disks have to be largely spaced in order to prevent interference with other optical elements. This results in an extended lens distance d and an increased thickness of the entire case 20. In addition, the prism itself would increase in weight, which may cause troubles to rotational control. Furthermore, the thick lens would have a deteriorated viewability during an eye examination (optometry).

To avoid the above problems, a Fresnel type prism provided with a stepped refractive angle (surface) is used as the rotary prisms 180a and 180b. This Fresnel type prism can provide the thickness almost equal to that of other lenses (2.5 mm or less). The auto-cross-cylinder lens 181 is also constructed of the Fresnel type prism to suppress the thickness. Similarly, the Fresnel type prism is adopted for the dispersion prism held in the disk 14.

It is to be noted that the increase in lens diameter causes an increase in disk diameter if the number of optical elements arranged in one disk is too large, which results in an enlarged size of the case 20. In the case of using optical elements each having an effective diameter of 35 mm, a preferable arrangement is to a maximum of six lenses in one disk. Thus, the disk can be maintained in an almost equal size to the conventional disk having twelve holes and an effective diameter of 19 mm.

By the above structure of the increased lens diameter and the suppressed lens distance d (the thickness of the case 20 in a direction of the optical axis 10), the visual angle α can be widened. This can reduce the peeping effect and give a sense of openness to the examinee, thereby lessen the intervention of accommodation. Thus, more accurate examination results can be obtained and the trial frame examination can be omitted. The increased lens diameter also allows the examiner to easily observe the examinee's eye through the test window 4 and check if the examinee is narrowing his eye. This helps in calling the examinee's attention for execution of more accurate examination.

In the present optometric apparatus, a distance between lenses placed in alignment with the optical axis 10 has been determined in design. Accordingly, power changes caused by a distance between apexes of plural lenses used in an overlapped state are compensated to provide an appropriate refractive power. More correct examination result can be obtained as compared with the examination using a trial frame.

During a near point examination, the right-and-left lens chamber units 2 are converged to inwardly direct the visual axes of both eyes of the examinee. At this time, the lens chamber units 2 are converged to such a degree that the units 2 do not interfere with each other, but there is a limit for the examinee whose pupillary distance is short. If the conventional lens of a small diameter (an effective diameter of 19 mm) is used, therefore, examination would inevitably be conducted in a state that an optotype for near point examination is hard to see for the examinee. On the other hand, the effective diameter and the visual angle of the lens in the present embodiment can be increased as compared with the conventional lens, so that the optotype for near point examination becomes easy to see, allowing execution of more accurate examination.

Figure 5:
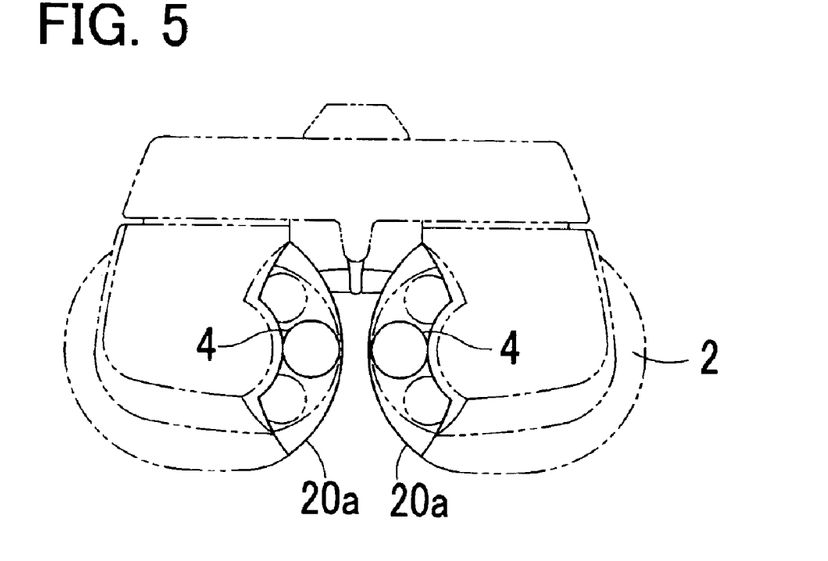
FIG. 5 is a view showing a partially transparent case of the lens chamber unit.

In addition to the increase in lens diameter of the optical element, a case cover 20a (indicated by a solid line in FIG. 5) of the lens chamber unit 2, constituting the periphery of the test window 4 (and also the test window 4' disposed on the examinee's side), is formed of a transparent member and similarly the internal disks 11 to 17 and the holder 151 and others which rotatably hold the lenses are constructed of transparent members. With this structure, the sense of openness can further be enhanced and the peering effect can be reduced. The case cover 20a has an identical shape on the examiner's side and the examinee's side. Accordingly, the examiner can easily observe facial expressions of the examinee through the case cover 20a. It is to be noted that at least the portions of the disks 11 to 17 covered by the case cover 20a may be formed of transparent members. Preferably, the transparent portions of the case cover 20a and the disks 11 to 17 are applied with antireflection films.

Figure 7:
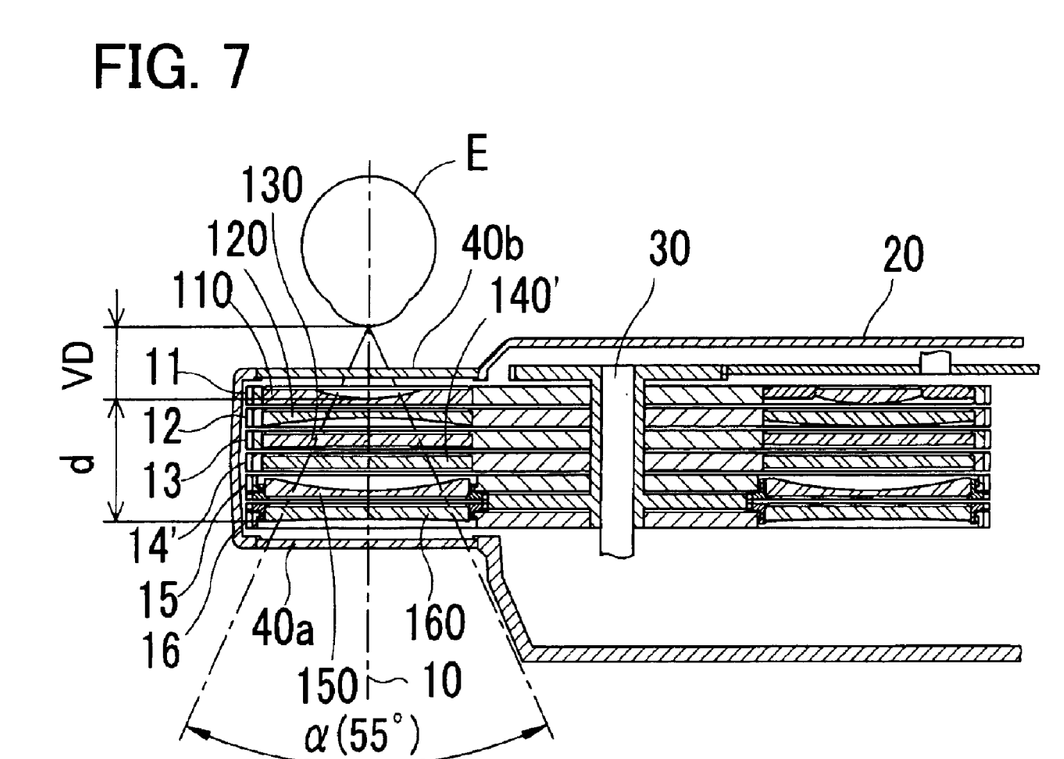
FIG. 7 is a view showing a modified example of the disk arrangement.

FIG. 7 is a modified example using six disks with respect to the structure shown in FIG. 2. In this structure, the second auxiliary lens disk 17 is eliminated and an auxiliary lens disk 14' holding a group of auxiliary lenses (AUX) 140' including the plain lens (PD), the pinhole (PH), an auto-cross-cylinder (AXC) of ±0.5D, the green filter (the red filter for the right eye), and the polarizing plate (Pola), which are arranged in five holes other than the opening, is arranged (see FIG. 8). The spherical lens disks 11, 12, and 13 and the cylindrical lens disks 15 and 16 are identical to those in FIG. 2 (FIG. 6). In FIG. 7, the lens distance d is shorter than that in FIG. 2, so that the visual angle α can be further widened Assuming d=21 mm, the visual angle becomes about 55°.

Explanation is made on an eye examination (optometry). Normally, each refractive power of a right eye and a left eye is examined. In an examination for one eye, the shielding plate BL (see FIG. 6 and FIG. 8) arranged in the disk 11 is used to shield the other eye under non-examination. In the conventional apparatus, the shielding plate BL is arranged in an auxiliary lens disk placed on the farther side from the spherical lens disk (this conventional arrangement is shown in FIG. 10). In this conventional case, disturbance light enters the inside of the lens chamber unit 2 through the test window 4' and thus movements of the spherical lenses and the superfluous internal structure may be seen by the examinee. This causes the examinee discomfort. Especially, when the case cover 20a is constructed of a transparent member, the movements of the spherical lenses and the superfluous structure could be viewed more easily. In this state, the examinee could not concentrate on the examination. In the apparatus in the present embodiment, on the other hand, the shielding plate BL is arranged in the high-power spherical lens disk 11 placed the closest to the examinee's eye. Accordingly, disturbance light can be prevented from entering the lens chamber unit 2. Even when the case cover 20a is constructed of a transparent member, the disturbance light is shielded in the closest position to the examinee's eye, which prevents the superfluous structure from being easily viewed by the examinee. In the case cover 20a formed of a transparent member, the shielding plate BL is preferably made of a frosted glass or a semitransparent material, not black.

Next explanation is made on how to produce spherical powers with the above lens structure.

Figure 8:
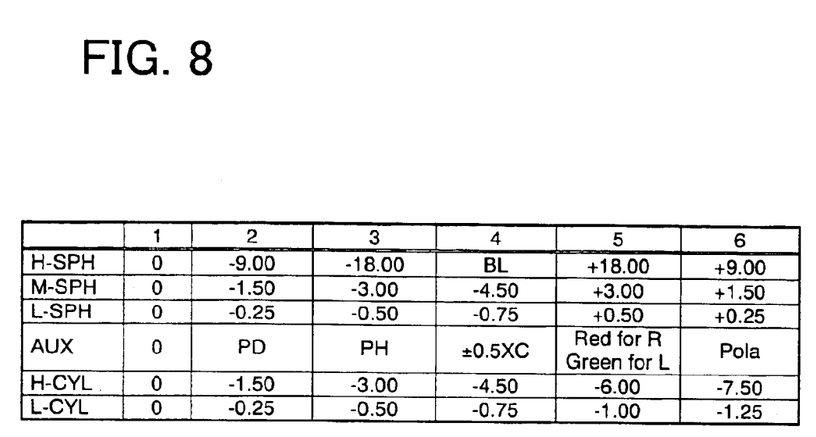
FIG. 8 is a table showing arrangements of optical elements in the disk arrangement in FIG. 7.

As mentioned above, the arrangement of spherical lenses in the conventional optometric apparatus with twelve holes in each spherical lens disk is for example as shown in FIG. 10. The conventional structure includes two spherical lens disks holding therein twenty-two spherical lenses and two openings in total. With the use of these lenses and openings, powers (diopters) of −19.00D to +16.75D can be produced in increments of 0.25D. However, the disk with twelve holes is liable to increase in size. Particularly, as the lens effective diameter is increased, the case of the lens chamber unit becomes larger in size. In the optometric apparatus in the present embodiment, therefore, as shown in FIGS. 6 and 8, three spherical lens disks 11 to 13 each having six holes are used to efficiently produce practical powers (−23.25D to +21.50D) in increments of 0.25D with the use of fourteen spherical lenses and three openings in total which are smaller in number than in the conventional apparatus.

Another arrangement of spherical lenses in the three spherical disks each having six holes is shown in FIG. 9. FIGS. 9A to 9E are tables showing lens arrangements in which the high-power spherical lens disk (H-SPH) 11 and the moderate-power spherical lens disk (M-SPH) 12 are the same in lens arrangement as those in FIG. 6 (FIG. 8), but the arrangement of the low-power spherical lens disk (L-SPH) 13 is different from that in FIG. 6 (FIG. 8). The lens arrangement of the lens disk 13 includes five spherical lenses whose powers are set from −1.25D to +1.25D in increments of 0.25D (wherein "0D" corresponds to the opening).

These are arranged to produce moderate-powers which are frequently used for myopia, without using the high-power lenses (arranged in the high-power disk 11). For instance, in the case of FIG. 6 (FIG. 8), the powers for myopia to −5.25D can be produced by the disks 12 and 13 ("−4.50D"+"0.75D"="−5.25D"). The spherical lenses in the disks 12 and 13 as arranged in FIG. 9A can produce powers for myopia of to −5.00D, those in FIG. 9B can produce powers of to −5.50D, those in FIG. 9C can produce powers of to −5.75D, those in FIG. 9D can produce powers of to −4.75D, and those in FIG. 9E can produce powers of to −4.50D.

Figure 9A:
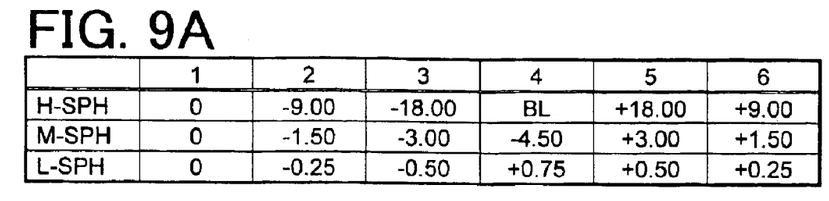
FIGS. 9A to 9G are tables showing modified examples of arrangements of spherical lenses in three spherical lens disks.
Figure 9B:
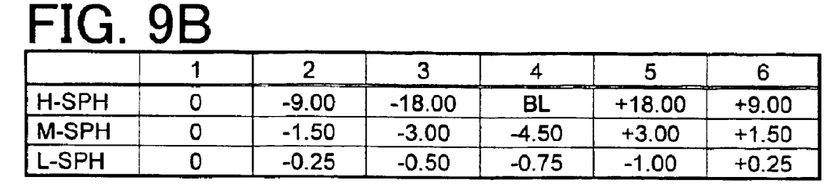
Figure 9C:
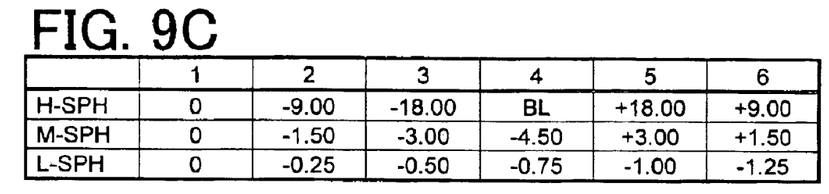
Figure 9D:
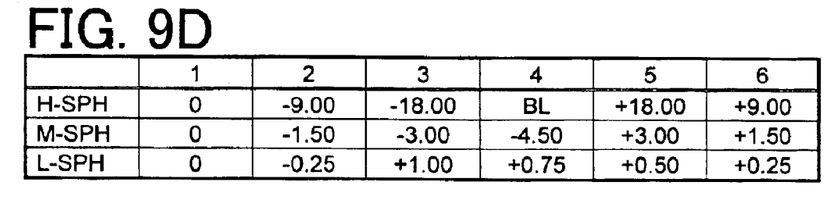
Figure 9E:
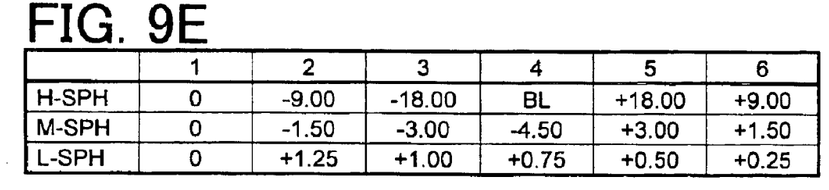
Figure 9F:
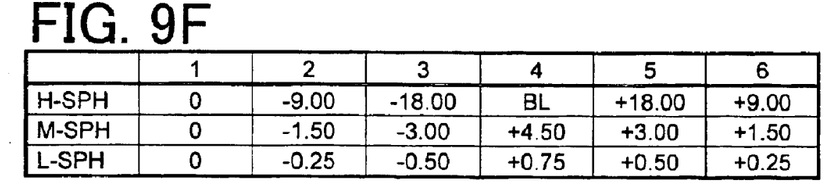
Figure 9G:
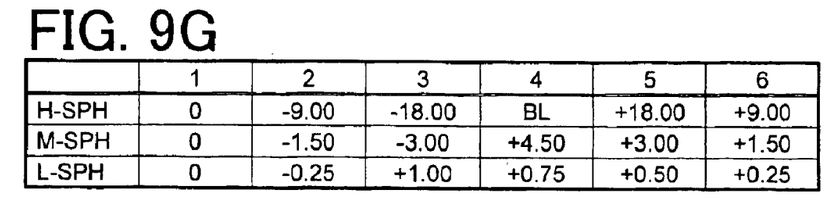

In the arrangements in FIGS. 9F and 9G, on the other hand, a combination of the disks 12 and 13 can only produce powers of to −3.50D and −3.25D respectively and it is disadvantageous to further produce higher powers for myopia because the high-power lenses in the disk 11 have to be combined. The combination of the high-power lenses having strong refractive powers, which may cause a deterioration in astigmatism and viewability, is preferably avoided as much as possible. The arrangements in FIG. 6 (FIG. 8) and FIGS. 9A to 9E, including the spherical lens of −4.50D in the disk 12, are advantageous when frequently used moderate-powers for myopia are regarded as important. Thus, high accurate examination can be executed.

As explained above, according to the present invention, a visual function of an examinee's eye can be accurately examined.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An optometric apparatus for a subjective examination of a visual function of an examinee's eye, comprising:
   a pair of right-and-left lens chamber units each having a test window; and
   rotary disks disposed in each unit, each disk holding therein optical elements and an opening or a lens of 0D as the optical element, one of the optical elements in each disk being placed between protective glasses of the test window of each unit,
   wherein the optical elements include large optical elements of 29 mm to 39 mm in effective diameter,
   a disk holding the large optical elements holds five to eight large optical elements,
   the disk disposed in a position farthest from the examinee's eye holds the large optical elements, and
   a visual angle is determined at 40° or more by the large optical element in the farthest disk.

2. The optometric apparatus according to claim 1, wherein the large optical elements include an optical element including an optical part having a predetermined optical characteristic and a transparent holder for holding the optical part, and the effective diameter is ensured by the optical part and the holder.

3. The optometric apparatus according to claim 1, wherein the large optical elements include a spherical lens, and the effective diameter is ensured by the spherical lens of a predetermined plus power and a transparent lens holder.

4. The optometric apparatus according to claim 1, wherein the disks include at least one disk holding spherical lenses, one disk holding cylindrical lenses, and one disk holding auxiliary lenses.

5. The optometric apparatus according to claim 1, wherein the disks include a first disk in which four spherical lenses of −18D, −9D, +9D, and +18D are arranged, a second disk in which five spherical lenses of −4.5D, −3D, −1.5D, +1.5D, +3D are arranged, and a third disk in which five spherical lenses selected from among lenses of −1.25D, −1D, −0.75D, −0.5D, −0.25D, +0.25D, +0.5D, +0.75D, +1D, and +1.25D are arranged so that diopters of the selected five lenses and zero diopter are set increasing in increments of 0.25D.

6. The optometric apparatus according to claim 5, wherein the first disk is disposed in a position closest to the examinee's eye and a shielding plate is arranged as the optical element in the first disk.

7. The optometric apparatus according to claim 1, wherein the large optical elements include a Fresnel type prism.

8. The optometric apparatus according to claim 1, wherein the disks are disks having a transparent portion around at least the optical elements, and the unit includes a case having a transparent portion around the test windows.

9. The optometric apparatus according to claim 1, wherein a shielding plate is arranged as the optical element in the disk disposed in the closest position to the examinee's eye.

10. The optometric apparatus according to claim 9, wherein the disks include spherical lens disks each holding therein spherical lenses as the optical elements, and the spherical lens disks are disposed in the closest position to the examinee's eye.

11. The optometric apparatus according to claim 10, wherein the spherical lenses in the closest disk has predetermined high power and a thickness of 30 mm or less.

12. The optometric apparatus according to claim 1, wherein the disks include three spherical lens disks each holding therein spherical lenses as the optical elements.

13. The optometric apparatus according to claim 1, wherein all disks hold the large optical elements.

* * * * *